(12) United States Patent
Gartside et al.

(10) Patent No.: US 7,888,541 B2
(45) Date of Patent: Feb. 15, 2011

(54) DOUBLE BOND HYDROISOMERIZATION OF BUTENES

(75) Inventors: Robert J. Gartside, Summit, NJ (US); Thomas P. Skourlis, Basking Ridge, NJ (US); Hassan Kaleem, Franklin Park, NJ (US)

(73) Assignee: Catalytic Distillation Technologies, Pasadena, TX (US)

( * ) Notice: Subject to any disclaimer, the term of this patent is extended or adjusted under 35 U.S.C. 154(b) by 1034 days.

(21) Appl. No.: 11/107,059

(22) Filed: Apr. 15, 2005

(65) Prior Publication Data

US 2006/0235252 A1 Oct. 19, 2006

(51) Int. Cl.
C07C 5/22 (2006.01)

(52) U.S. Cl. ............... 585/253; 582/324; 582/332; 582/646; 582/647; 582/664; 582/670

(58) Field of Classification Search ............ 585/253, 585/324, 332, 646, 647, 664, 670
See application file for complete search history.

(56) References Cited

U.S. PATENT DOCUMENTS

| | | | |
|---|---|---|---|
| 3,531,545 A | 9/1970 | Garner et al. ............ 260/683.2 |
| 3,751,502 A | 8/1973 | Hayes | |
| 3,872,178 A * | 3/1975 | Tabler ...................... 585/378 |
| 4,268,701 A | 5/1981 | Dang Vu et al. | |
| 4,417,089 A | 11/1983 | Drake ...................... 585/670 |
| 4,911,822 A | 3/1990 | Franck et al. ............... 208/66 |
| 5,087,780 A | 2/1992 | Arganbright ............... 585/259 |
| 5,281,753 A | 1/1994 | Olson et al. | |
| 5,595,634 A * | 1/1997 | Hearn et al. ................ 203/29 |
| 5,609,654 A | 3/1997 | Le et al. .................... 44/449 |
| 5,969,203 A | 10/1999 | Dorbon et al. ............. 585/324 |
| 6,072,091 A | 6/2000 | Cosyns et al. ............. 585/259 |
| 6,242,661 B1 | 6/2001 | Podrebarac et al. | |
| 6,333,442 B1 | 12/2001 | Cosyns et al. | |
| 6,420,619 B1 | 7/2002 | Gartside et al. ............ 585/324 |
| 6,583,329 B1 | 6/2003 | Podrebarac | |
| 6,686,510 B2 | 2/2004 | Commereuc et al. ........ 585/324 |

(Continued)

FOREIGN PATENT DOCUMENTS

WO WO 93/21137 * 10/1993

OTHER PUBLICATIONS

PCT International Search Report (2 Pages).

(Continued)

*Primary Examiner*—Tam M Nguyen
(74) *Attorney, Agent, or Firm*—Osha • Liang LLP

(57) ABSTRACT

A process is disclosed for the preferential conversion to 2-butene of a C4 stream containing 1-butene and 2-butene. The process involves mixing the C4 stream with a first hydrogen stream to form a feed stream, hydroisomerizing the feed stream in the presence of a first hydroisomerization catalyst in order to convert at least a portion of the 1-butene to 2-butene, thereby producing a hydroisomerization effluent, separating the hydroisomerization effluent in a fractionation column having an upper end and a lower end to form a 1-butene mixture at the upper end, a top effluent stream containing isobutane and isobutylene and a bottoms stream containing 2-butene, and hydroisomerizing the 1-butene mixture at the upper end of the column using a second hydroisomerization catalyst. A corresponding apparatus also is disclosed.

23 Claims, 6 Drawing Sheets

U.S. PATENT DOCUMENTS

| | | | |
|---|---|---|---|
| 6,777,582 B2 | 8/2004 | Gartside et al. | 585/324 |
| 6,872,862 B2 * | 3/2005 | Bridges et al. | 585/324 |
| 2002/0169346 A1 | 11/2002 | Commereuc et al. | |

OTHER PUBLICATIONS

Written Opinion of the International Searching Authority (6 Pages).

Official Action from Patent Office of the Russian Federation Communication; Application No. 2007142195/04(046191); dated Nov. 7, 2008; 10 pages.

Official Action and International Search Report in Singapore Patent Application No. 200716845-3; dated Oct. 20, 2008; 8 pages.

Notice of Preliminary Rejection in Korean Patent Application No. 10-2007-7026418 dated Apr. 7, 2009, 5 pages.

Singaporean Official Action issued in Application No. 200716845-3 dated Jun. 19, 2009 (7 pages).

Examination Report issued in Application No. GCC/P/2006/6106 dated Jan. 5, 2009 (4 pages).

Extended European Search Report from related European Application No. 06749592.9 dated Dec. 12, 2009. (5 pages).

Examination Report issued Apr. 5, 2010 by the Intellectual Property Office of Singapore in corresponding application No. 200716845-3 (7 pages).

Office Action dated Mar. 31, 2010 issued by the Canadian Intellectual Property Office in corresponding Canadian application No. 2,604,094 (2 pages).

Translation of First Office Action issued Jul. 30, 2010 in corresponding Chinese Patent Application No. 200680012442.1 (13 pages).

Office Action {Notice of Grounds for Rejection} issued in corresponding Japanese Patent Application No. 2008-506555 (5 pages).

* cited by examiner

US 7,888,541 B2

DOUBLE BOND HYDROISOMERIZATION OF BUTENES

FIELD OF THE INVENTION

The present invention is directed to double bond hydroisomerization of C4 olefins.

BACKGROUND OF THE INVENTION

In many processes it is desirable to have isomerization of double bonds within a given molecule. Double bond isomerization is the movement of the position of the double bond within a molecule without changing the structure of the molecule. This is different from skeletal isomerization where the structure changes (most typically representing the interchange between the iso form and the normal form). Skeletal isomerization proceeds by a completely different mechanism that double bond isomerization. Skeletal isomerization typically occurs using a promoted acidic catalyst.

There are two basic types of double bond isomerization, namely hydroisomerization and non-hydroisomerization. The former uses small quantities of hydrogen over noble metal catalysts (such as Pt or Pd) and occurs at moderate temperatures while the latter is hydrogen free and typically employs basic metal oxide catalysts at higher temperatures.

Double bond hydroisomerization at moderate temperatures is mostly used to maximize the interior olefin (2-butene for example as opposed to 1-butene) since the thermodynamic equilibrium favors the interior olefin at lower temperatures. This technology is used when there is a reaction that favors the interior olefin over the alpha olefin. Ethylenolysis of 2-butene to make propylene is such a reaction. The ethylenolysis (metathesis) reaction is 2-butene+ethylene→propylenes. Mixed normal butenes (1- and 2-butenes) are reacted to maximize the 2 butenes and thus maximize propylene. Ethylene and 1-butene do not react. If in a mixture of C4 normal olefins, 2-butene can be maximized, then the reaction to propylene will be maximized.

It is well known that double bond hydroisomerization reactions occur simultaneously with hydrogenation reactions. In many commercial applications, a feedstock with highly unsaturated molecules (acetylenics and/or dienes) is processed over a fixed bed of supported noble metal catalyst in the presence of hydrogen. For example, the reaction of butadiene over noble metal catalysts can be summarized in the reaction sequence shown below:

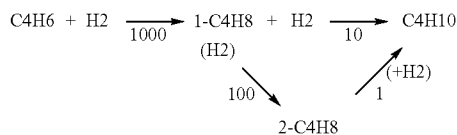

The primary hydrogenation reaction of butadiene plus hydrogen forms 1-butene. It proceeds rapidly over the catalysts (relative rate equivalent to 1000). In the presence of hydrogen, two reactions occur with 1-butene. One is the hydroisomerization to 2-butene (relative rate of 100). This reaction requires the presence of hydrogen to proceed but does not consume hydrogen. The other reaction is hydrogenation to normal butane (relative rate of 10). The final reaction is the hydrogenation of 2-butene directly to normal butane. This is the slowest reaction (relative rate of 1) and essentially can be neglected. Under normal conditions over noble metal catalysts, it is expected that the selectivity of 1-butene conversion will be 90% to 2-butene and 10% to n-butane. The latter represents a loss of olefins and is undesirable.

Hydroisomerization and hydrogenation reactions are known to be carried out in fixed bed reactors. U.S. Pat. No. 3,531,545 describes a process and method for double bond isomerization consisting of mixing a hydrocarbon stream containing 1-olefins and at least one sulfur-containing compound with hydrogen, heating the mixed hydrocarbon/hydrogen stream to reaction temperatures, contacting the stream with a noble metal catalyst, and then recovering the 2-olefins as a product. The process described in this patent utilizes sulfur as an additive to reduce the hydrogenation tendency of the catalyst and thus increase hydroisomerization. Sulfur is shown to be either present in the feed, added to the feed, or added to the hydrogen stream.

It is known to employ a hydrocarbon fractionation tower in combination with a fixed bed hydrogenation reactor. In U.S. Pat. No. 6,072,091, a distillation column is used in combination with at least one hydrogenation reaction zone. The hydrogenation reaction zone is associated with the rectification section of the distillation column. More specifically, hydrocarbons are removed from the rectification section of the column to hydrogenate at least a portion of the acetylenic and diolefinic hydrocarbons contained therein. The effluent from the reaction zone is then re-introduced into the rectification section of the distillation column.

It is known to carry out a hydroisomerization reaction within a catalytic distillation tower. In U.S. Pat. No. 5,087,780 (Arganbright), a process for the isomerization of butenes in a mixed C4 hydrocarbon stream is described. A stream containing 1-butene, 2-butene, and small amounts of butadiene is fed to a catalytic distillation tower containing a Pd catalyst. A small amount of hydrogen is also fed to the tower. The 1-butene, being among the most volatile of the C4s, moves overhead while the 2-butene, being less volatile, tends to go toward the bottom of the tower. Catalyst is located in the zone with higher concentrations of 2-butene, and hydroisomerization of 2-butene to 1-butene occurs. Residual 2-butene in the bottom may be recycled to the tower. If isobutylene is part of the feed mixture, it will also go overhead with the 1-butene.

In U.S. Pat. No. 6,242,661 a process for the separation of isobutylene from normal butenes is disclosed. This process also employs a catalytic distillation process incorporating the hydroisomerization reaction. A mixture of normal and isobutylenes is fed to a tower along with a small amount of hydrogen. The tower contains a Pd catalyst located within distillation structures within the tower. In this process, the catalyst is located in the upper section of the tower in a multiplicity of catalyst beds. As the fractionation occurs, the isobutylene moves overhead. 1-Butene (also a volatile component) tends to move with isobutylene. Since the system does not employ a skeletal isomerization catalyst, the isobutylene moves through the tower unaffected. However, hydroisomerization occurs in the regions of high 1-butene and the 1-butene is converted to 2-butene. This 2-butene is less volatile and moves to the bottom of the tower. In this fashion, relatively pure isobutylene is obtained overhead since the 1-butene is reacted and moves to the bottom as 2-butene.

The above processes all produce a stream that is concentrated in 2-butene. In the ethylenolysis (metathesis) reaction of 2-butene to form propylene, it is known that isobutylene is not a desired feed component. Isobutylene and ethylene will not react. Isobutylene and 2-butene will react to form propylene and 2-methyl-2-butene. This reaction has a negative effect on the propylene selectivity of the ethylenolysis reaction and is not desirable. Thus in most cases, it is preferable to remove isobutylene from a 2-butene stream prior to reaction with ethylene.

It is known to use a catalytic distillation-deisobutylenizer (CD-DeIB) to prepare a 2-butene stream for a metathesis (ethylenolysis) reactor. Similarly to U.S. Pat. No. 6,242,661 referenced above, a CD-DeIB will remove isobutylene overhead while maximizing the flow of 2-butene out the bottoms as the 1-butene is hydroisomerized to form 2-butene. The tower typically contains alternating catalyst and fractionation structures above the feed point, and fractionation structures below the feed point. Usually there are about four catalyst sections in the tower. Hydrogen is added below the feed point in order that it is sufficiently dispersed by the time it reaches the feed point.

The CD-DeIB in this service accomplishes two functions. It hydroisomerizes the 1-butene to 2-butene to improve recovery of 2-butene and maximize the production of propylene, and also hydrogenates the small remaining amounts of butadiene after the selective hydrogenation to reduce the content of butadiene, which is a poison for the metathesis catalyst. In a CD-DeIB tower, the isobutane and isobutylene are the most volatile components and tend to go overhead in the tower. The 2-butene and the n-butane are the least volatile and tend to go to the bottom. The 1-butene and butadiene have intermediate volatility and will go up or down depending upon the operation of the tower. If the tower is designed so that the 1-butene goes up, it contacts a catalyst section and is hydroisomerized to 2-butene to the limit of the 1-butene/2-butene equilibrium in the tower. The 2-butene formed from hydroisomerization of the 1-butene tends to move downward and the remaining 1-butene continues to move upward. The fractionation sections of the tower separate the 2-butene from the 1-butene.

The butadiene which enters the CD-DeIB is slightly less volatile than the 1-butene. Some of the butadiene moves upward where it is hydrogenated over the catalyst. The primary product of the hydrogenation is 1-butene. However, a portion of the butadiene that moves upward is "fully" hydrogenated to n-butane. This constitutes a loss of n-butenes and thus a loss of feed for a metathesis unit. Some of the butadiene moves downward with the primarily 2-butene product. This butadiene is unreacted since it does not come into contact with catalyst. Butadiene can be present in no more than very low levels in the bottoms if the 2-butene is to be fed to a metathesis unit.

U.S. Pat. No. 6,420,619 is directed to a process in which both a "back end" catalytic distillation-hydrogenation unit and a catalytic distillation deisobutylenizer are employed. This concept replaces the fixed bed selective hydrogenation units normally associated with ethylene plant fractionation systems. There are typically separate fixed bed units for the C3, C4 and C5 fractions to remove the acetylenics and diolefins to low levels prior to further processing. The system of U.S. Pat. No. 6,420,619 uses a C3 to C6 hydrocarbon feedstock from a steam cracker or FCC unit. In the "back end" CDHydro section, catalytic distillation towers are used to hydrogenate acetylenics and diolefins in the stream including butadiene, methyl acetylene and propadiene and produce a propylene product stream. The bottoms of the tower produces a $C_4+$ stream which is then sent to a fractionation system which includes a debutanizer. The $C_4$ overhead stream from the debutanizer is routed to a CD-DeIB where hydroisomerization occurs. In addition to the $C_4$ feed to the debutanizer, there is a $C_5+$ recycle from the downstream fractionation system following the metathesis unit.

Three advantages of the system disclosed in U.S. Pat. No. 6,420,619 are:

1. recycle of the $C_5+$ stream from the metathesis unit allows for a higher recycle conversion of the butenes since the conventional system uses a C4 side draw from the depropylenizer which is intended to recycle unconverted 2-butene back to the metathesis reactor,
2. the removal of heavies prevents buildup in the recycle stream, and
3. a catalyst can be used in the debutanizer that also can be used to selectively remove any traces of butadiene.

One disadvantage of a conventional CD-DeIB system is that large quantities of catalyst must be used. Another disadvantage, as indicated above, is that in order to saturate the butadiene, the fractionation tower must be designed to push the butadiene up over the catalyst. This results in a large, costly tower with very high reflux. A third disadvantage is that when the tower bottoms is to be used as a feed stream for a metathesis unit, the quantity of isobutylene in the bottoms is required to be low, thereby resulting in very high utility costs for reboiling and condensing.

An alternative to a CD-DeIB for obtaining a 2-butene feed steam is a system which employs a fixed bed hydroisomerization unit downstream from a selective hydrogenation unit. The selective hydrogenation unit first removes butadiene to low levels. Then the effluent C4 feed stream is fed to a second fixed bed reactor and hydrogen is introduced. In the fixed bed unit the 1-butene in the stream hydroisomerizes to 2-butene and the small amount of butadiene that remains reacts. The effluent then goes to a conventional fractionating tower where the isobutylene and isobutane are separated overhead and the 2-butene goes out the bottom where it enters a disengaging drum in which any excess hydrogen is vented. The remainder of the bottoms is used as feed for the metathesis unit. This process requires less catalyst than the CD-DeIB unit because of higher driving forces for the fixed bed. The fractionating tower can be designed to allow more isobutylene to pass into the bottoms effluent, thus saving on utilities and capital since a smaller tower can be used. The disadvantage of the fixed bed system is that the quantity of n-butenes recovered is slightly lower than when a CD-DeIB is used.

U.S. Pat. No. 6,686,510 is directed to the production of high-purity isobutylene and propylene from hydrocarbon fractions having four carbon atoms. The process disclosed in this document comprises three successive stages, namely 1) the selective hydrogenation of butadiene with isomerization of 1-butene into 2-butene up to thermodynamic equilibrium; 2) the separation by distillation into a top fraction containing isobutylene and a bottom fraction containing 2-butene and butane, and 3) the metathesis of the 2-butene fraction with ethylene to produce propylene.

Thus, various systems are known for preparing 2-butene streams for use as feed streams for a metathesis unit. It would be useful to develop a method and apparatus for the selective hydroisomerization of 1-butene to 2-butene which has improved efficiency over prior known systems.

SUMMARY OF THE INVENTION

According to the invention, a double bond hydroisomerization process for increasing the selectivity of 2-butene over 1-butene is provided. The invention increases the yield of 2-butenes from a given C4 feed stream and produces a 2-butene stream containing a lower concentration of butadiene, thereby resulting in less fouling of the catalyst during a subsequent process such as metathesis.

The invention in a preferred form is a process for the preferential conversion to 2-butene of a C4 stream containing 1-butene and 2-butene, comprising mixing the C4 stream with a first hydrogen stream to form a feed stream, hydroisomerizing the feed stream in the presence of a first hydroisomerization catalyst in order to convert at least a portion of the 1-butene to 2-butene, thereby producing a hydroisomerization effluent, separating the hydroisomerization effluent in a fractionation column to form a 1-butene mixture at the upper end, a top effluent stream comprising isobutane and isobutylene and a bottoms stream comprising 2-butene, and hydroisomerizing the 1-butene mixture at the upper end of the column using a second hydroisomerization catalyst to obtain additional 2-butene in the bottoms stream. Hydroisomerization takes place at an elevation in the column at which the 1-butene concentration would be at a maximum if this further hydroisomerization step using the second hydroisomerization catalyst were eliminated.

In one preferred embodiment, the feed stream comprises butadiene, and the method further comprises the step of hydrogenating the feed stream before hydroisomerization to reduce the butadiene content of the C4 stream to no more than about 1 wt %. The second hydroisomerization catalyst is usually located within the fractionation tower and often is positioned within distillation structures.

In another form, the method further comprises mixing the bottoms stream with a suitable metathesis reactant to form a metathesis feed stream, and feeding the metathesis feed stream to a metathesis reactor and reacting the 2-butene with the metathesis reactant to form a metathesis product. Usually, the metathesis reactant comprises ethylene and the metathesis product comprises propylene.

Sometimes the feed stream includes C5 and heavier components, and the method further comprises removing the C5 and heavier components from the hydroisomerization effluent prior to fractionation. In some cases, the bottoms stream or the metathesis feed stream is purified before the metathesis feed stream is sent to the metathesis reactor.

In yet another embodiment, a second hydrogen stream is fed to the hydroisomerization reactor at a location downstream from the feed point of the first hydrogen stream. In some cases, a third hydrogen stream is fed to the fractionation column at a location downstream from the feed point of the second hydrogen stream. One, two or all three of the hydrogen streams may further comprise carbon monoxide.

In another form, the method further comprises the step of separating the metathesis product from heavier components to form a heavy component stream and combining the heavy component stream with the hydroisomerization effluent.

Usually, the top stream and the bottoms stream each contain small quantities of 1-butene. In some cases, the flow rate of 1-butene in the top stream is greater than the flow rate of 1-butene in the bottoms stream. In other cases, the flow rate of 1-butene in the bottoms stream is greater than the flow rate of 1-butene in the top stream.

Typically, the first and/or second hydroisomerization catalyst comprises a group VIIIA metal on a support. In some cases, an additive selected from the group consisting of gold, silver and alkali metals is also included. The first and second catalysts can contain the same or different metals at the same or different loadings.

Another embodiment is an apparatus for the preferential conversion to 2-butene of a feed stream containing 1-butene and 2-butene. The apparatus comprises a hydroisomerization reactor configured to contain a first hydroisomerization catalyst for converting at least a portion of the 1-butene in the feed stream to 2-butene and to form a hydroisomerization effluent, and a fractionation column having an upper end and a lower end. The fractionation column is configured to separate the hydroisomerization effluent to form a 1-butene mixture at the upper end, a top effluent stream comprising isobutane and isobutylene, and a bottoms stream comprising 2-butene. A hydroisomerization catalyst stage is disposed at the upper end of the fractionation column to further hydroisomerize the 1-butene mixture to form 2-butene.

The invention accordingly comprises the several steps and the relation of one or more of such steps with respect to each of the others and the article possessing the features, properties and relation of elements exemplified in the following detailed disclosure.

DETAILED DESCRIPTION OF THE INVENTION

The invention provides an apparatus and method for obtaining improved yields of 2-butene from a C4 stream as compared to prior known techniques. A fixed bed hydroisomerization reactor is used upstream from a deisobutylenizer which has a catalyst stage at the point at which the driving force for the hydroisomerization reaction is high. These embodiments will be described below in further detail.

Figure 1:
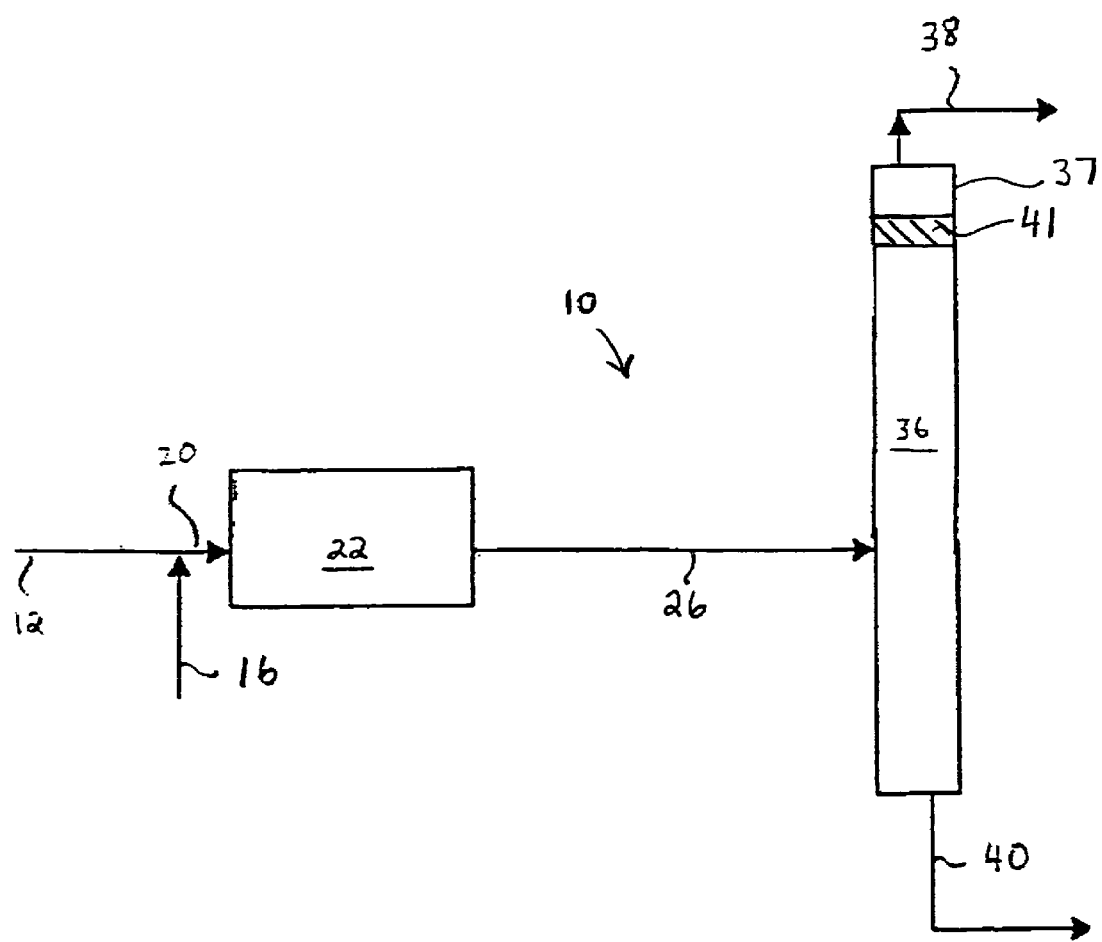
FIG. 1 is a schematic drawing of a first embodiment in which a 2-butene stream is produced.

Referring to the drawings and first to FIG. 1, an apparatus and process are shown for producing a 2-butene stream from a C4 feed stream. The overall process is designated as 10. A C4 feed stream, which is designated as 12, is fed to a fixed bed hydroisomerization reactor 22. A typical C4 feed stream to the hydroisomerization reactor 22 contains 2-50 parts by weight 1-butene, 2-50 parts by weight 2-butene, 2-50 parts by weight isobutylene, 2-50 parts by weight isobutane, 2-50 parts by weight n-butane and 0-1 part by weight butadiene, the total parts by weight being 100. In many cases, butadiene is no more than 1500 ppmw. Hydrogen in stream 16 is fed directly to the hydroisomerization reactor 22 or is combined with stream 12 to form stream 20. In the hydroisomerization reactor 22, 1-butene is hydroisomerized into 2-butene using any suitable hydroisomerization catalyst. Examples of such catalysts are noble metals (ca. Pd) supported on alumina. Additives to the metals including Ag, Au, etc can be used to modify the reaction characteristics. Typical reactor pressures are 2-30 barg and usually 5-18 barg. Typical reactor inlet temperatures are 80-250 Deg. F. and usually 120-180 Deg. F. The reactor effluent, in stream 26, is fed to a deisobutylenizer tower 36. Typical tower temperatures are 80-220 Deg. F. and usually 100-160 Deg. F. Typical reactor pressures are 2-12 barg and usually 3-8 barg. The reactor effluent 26 optionally may be vented to remove excess hydrogen from the stream before being fed to the deisobutylenizer tower 36. The top stream 38 from the deisobutylenizer tower 36 contains isobutylene and isobutane, and small quantities of 1-butene and 2-butene. The bottoms stream 40 contains most of the 2-butene.

To further hydroisomerize the remaining 1-butene to 2-butene in the deisobutylenizer tower 36, a catalyst section 41, which preferably is a single catalyst stage, is included at the upper end 37 of the deisobutylenizer tower 36. It is important that the single catalyst stage be located within the section of high driving force for the hydroisomerization reaction. Depending on the tower operation this typically is the upper end 37 of the deisobutylenizer tower 36. A single catalyst stage is that quantity of catalyst required to react the remaining 1-butene at that high driving force location within the tower to an equilibrium mixture of 1-butene and 2-butene. The type of catalyst used can be the same as, or different from, the catalyst used in the hydroisomerization reactor 22 and can be installed in one or more beds. The 2-butene formed in this hydroisomerization reaction moves downwardly through the deisobutylenizer tower 36 and out in the bottoms stream 40. The embodiment of FIG. 1 converts more of the 1-butene originating in the C4 feed stream 12 into 2-butene than a conventional system in which no catalyst section 41 is included in the deisobutylenizer tower 36.

The catalyst section 41 preferably is positioned at the elevation in deisobutylenizer tower 36 at which the 1-butene concentration would be at a maximum if no catalyst section 41 were included. Typically, this is near the top of the column. To determine the appropriate elevation for the catalyst section 41 in a particular system, the point of maximum driving force for the hydroisomerization reaction is determined at the conditions under which the fractionator is set to operate. The reaction between 1-butene and 2-butene can be represented by equation (1) where B1 is 1-butene, B2 is 2-butene, $k_{b1}$ is the reaction k for B1 to B2 and $k_{b2}$ is the reaction k for B2 to B1.

(1)

The rate of reaction is the reaction k times the concentration of the reactant. The ratio of the reaction k's, the equilibrium coefficient $K_{eq}$, is equal to the ratio of $k_{b1}$ to $k_{b2}$. The rate of the disappearance of B1 via hydroisomerization from B1 to B2 is:

Rate=$-k_{b1}[B1]+k_{b2}[B2]$

Where [B1] and [B2] are the mole percentages of 1-butene and 2-butene respectively. The driving force for the conversion of B1 to B2 can be defined by dividing both sides by $-k_{b1}$ resulting in the following:

Driving force=$[B1]-([B2]/K_{eq})$.

This driving force factor can be plotted as a function of position in the tower for a particular system and is the preferred technique for locating the optimal point for the side draw location.

Figure 2:
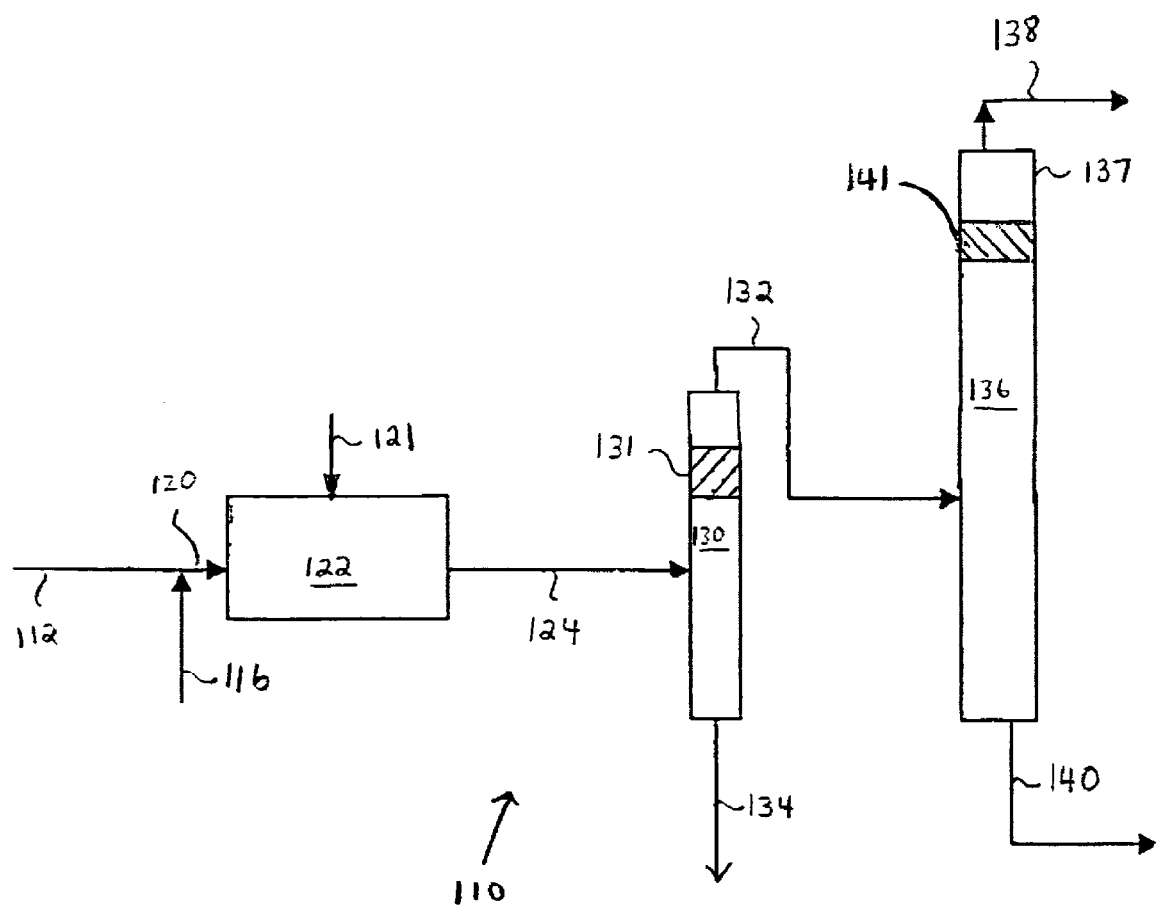
FIG. 2 is a schematic drawing of a second embodiment in which a 2-butene stream is produced, with C5+ compounds being removed prior to fractionation of the C4 compounds.

Referring next to FIG. 2, another embodiment is shown for producing a 2-butene stream from a C4 feed stream in which a catalyst section is included in a deisobutylenizer. In this embodiment, C5+ compounds are removed upstream from the deisobutylenizer tower. Furthermore, the production of butanes during the hydroisomerization reaction is minimized by the use of multiple hydrogen feed streams and/or the inclusion of small quantities of carbon monoxide in one or more of the hydrogen streams. The inventors have surprisingly found that CO acts as an inhibitor for the hydrogenation reactions of butenes to butanes while allowing the double bond hydroisomerization reactions to continue. By feeding the hydrogen or the hydrogen/CO mixture at multiple locations along the length of a fixed bed reactor, butadiene in the feed is hydrogenated to butenes while at the same time hydrogenation of butenes to butanes is minimized. It is noted that the use of one or more streams containing H2 and CO also can be used in the embodiment shown in of FIGS. 1, 3 and 4.

The system shown in FIG. 2 is designated as 110. A C4 feed stream, which is designated as 112, is fed to a fixed bed hydroisomerization reactor 122. A stream 116 containing either just hydrogen, or a mixture of hydrogen and carbon monoxide, is fed directly to the hydroisomerization reactor 122 or is combined with stream 112 to form stream 120. Hydrogen and/or carbon monoxide optionally also can be injected into the reactor 122 at a second location approximately midway along the length of the reactor 122 is stream 121. In the hydroisomerization reactor 122, 1-butene is hydroisomerized into 2-butene, forming reactor effluent stream 124. Stream 124 is fed to a first fractionating tower 130. The effluent stream 124 optionally may be vented to remove excess hydrogen before being fed to the first fractionating tower 130. In the first fractionating tower 130, C4 compounds are removed from the top in stream 132 and C5+ compounds are removed as bottoms in stream 134. A hydrogenation catalyst bed 131, also known as a "guard bed", hydrogenates remaining butadienes to form butenes. The hydrogen for this reaction is preferentially the residual hydrogen from the hydroisomerization in reactor 122.

Stream 132 is subsequently fed to a deisobutylenizer tower 136. The top stream 138 from the deisobutylenizer tower 136 contains isobutylene and isobutane, and small quantities of 1-butene and 2-butene. The bottoms stream 140 contains the 2-butene. Above the feed point in deisobutylenizer tower 136, there is an elevation at the upper end 137 of the deisobutylenizer tower 136 at which the concentration of 1-butene is at a maximum if no catalyst section is included in the deisobutylenizer tower 136. A catalyst section 141 is positioned at this location to hydroisomerize additional 1-butene to form 2-butene. The location of the catalyst section 141 preferably is selected in the same manner as in the embodiment of FIG. 1, i.e. the elevation at which the driving force for the hydroisomerization reaction is a maximum if no hydroisomerization had occurred. This is the elevation at which B1−(B2/Keq) is maximized.

Figure 3:
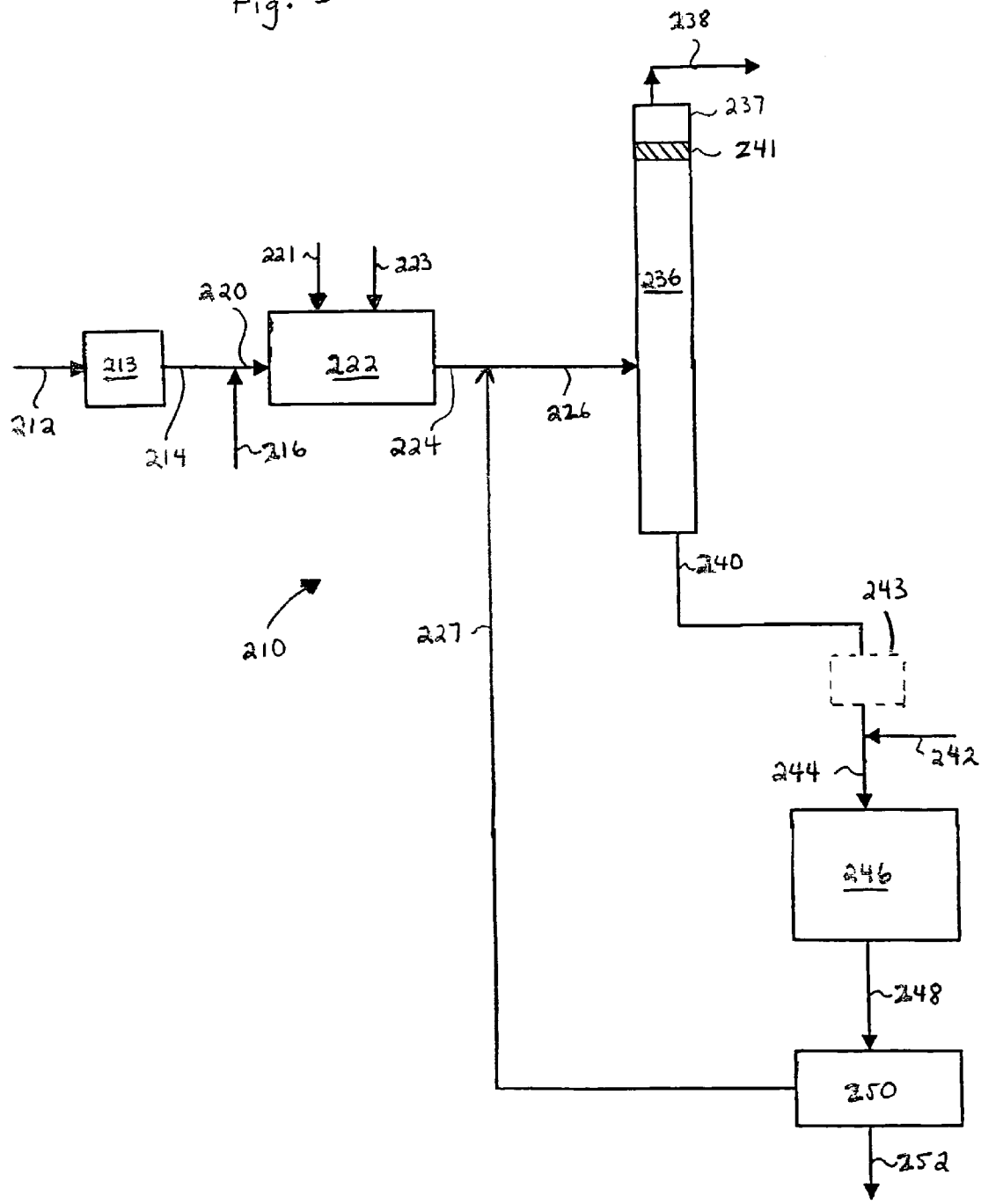
FIG. 3 is a schematic drawing of an embodiment in which a 2-butene stream is produced and used as the feed stream in a metathesis reaction.

Referring next to FIG. 3, a process for producing propylene is shown in which a fixed bed hydroisomerization reactor is used upstream from a DeIB having a single catalytic stage near the top of the tower. The system shown in FIG. 3 is designated as 210. A C4 feed stream, which is designated as 212, is passed through a selective hydrogenation unit 213 which hydrogenates butadiene in the presence of a hydrogenation catalyst, producing a low-butadiene C4 feed stream 214. Stream 214 is fed to a fixed bed hydroisomerization reactor 222. Hydrogen in stream 216 is fed directly to the hydroisomerization reactor 222 or is combined with stream 214 to form stream 220. Carbon monoxide optionally is included in the hydrogen stream 216. Hydrogen and optionally also carbon monoxide can be injected in the reactor 222 at a second location approximately one third of the way along the length of the reactor 222 in stream 221 and at a third location about two thirds of the way along the length of the reactor 222 in stream 223. If multiple points of injection are used, the volume of the hydrogen and optional carbon monoxide introduced in stream 216 is reduced in order that the overall volume of hydrogen and CO is no more than is necessary to achieve the desired result. The advantage of splitting the hydrogen into two different feed points is to reduce the production of butanes in the reactor 222. The advantage of including carbon monoxide in streams 216 and/or 223 is to inhibit hydrogenation reactions while allowing hydroisomerization reactions to proceed.

When a single injection of a mixed H2/CO stream is used, the CO and H2 preferably are injected at a single point upstream from the hydroisomerization reactor. In this case, the CO to H2 ratio is between 0.1% and 3% on a molar basis, more preferably 0.1-0.5%, and is typically 0.2-0.4% on a molar basis. When multiple injections are used, as are depicted in FIGS. 2 and 3, hydrogen preferably is apportioned at each feed point in a manner such that the total volume of the catalyst in the hydroisomerization reactor is in an active state. The ratio of CO to H2 at each point of injection preferably, but not necessarily, is the same as at the other points of injection. It is also feasible to have one of the streams contain only hydrogen. The split feed of hydrogen and the inclusion of carbon monoxide can be used in any of the embodiments of FIGS. 1-4.

In the hydroisomerization reactor 222, 1-butene is hydroisomerized into 2-butene. The reactor effluent stream 224 is combined with a metathesis recycle stream 227 to form stream 226. The effluent stream 224 optionally may be vented to remove excess hydrogen from the stream before being combined with the metathesis recycle stream 227. Stream 226 is fed to a deisobutylenizer tower 236. Above the feed point in deisobutylenizer tower 236, there is an elevation at the upper end 237 of the deisobutylenizer tower 236 at which the concentrations of 1-butene is at a maximum if no catalyst section is included. A catalytic section 241 which preferably is a single catalyst stage is positioned at this location in order to hydroisomerize the remaining 1-butene to 2-butene. The top stream 238 from the deisobutylenizer tower 236 contains isobutylene and isobutane, and small quantities of 1-butene and 2-butene. The bottoms stream 240 contains most of the 2-butene. Preferably, the butadiene content of stream 240 is less than 50 parts per million based on weight, and more preferably less than 10 parts per million based on weight, since butadiene is a poison for metathesis catalysts. Stream 240 optionally is purified in one or more guard beds 243. An ethylene feed stream 242 is combined with the bottoms stream 240 to form a metathesis reactor feed stream 244. This stream enters the metathesis reactor 246, in which the 2-butene and ethylene react to form a metathesis product stream 248.

The metathesis product stream 248 contains propylene, butenes and C5+ hydrocarbons. The propylene is separated from the heavier hydrocarbons in separator 250 and is removed as the product in stream 252. The C4, C5 and heavier hydrocarbons are recycled in metathesis recycle stream 227 and are combined with stream 224 in stream 226.

Figure 4:
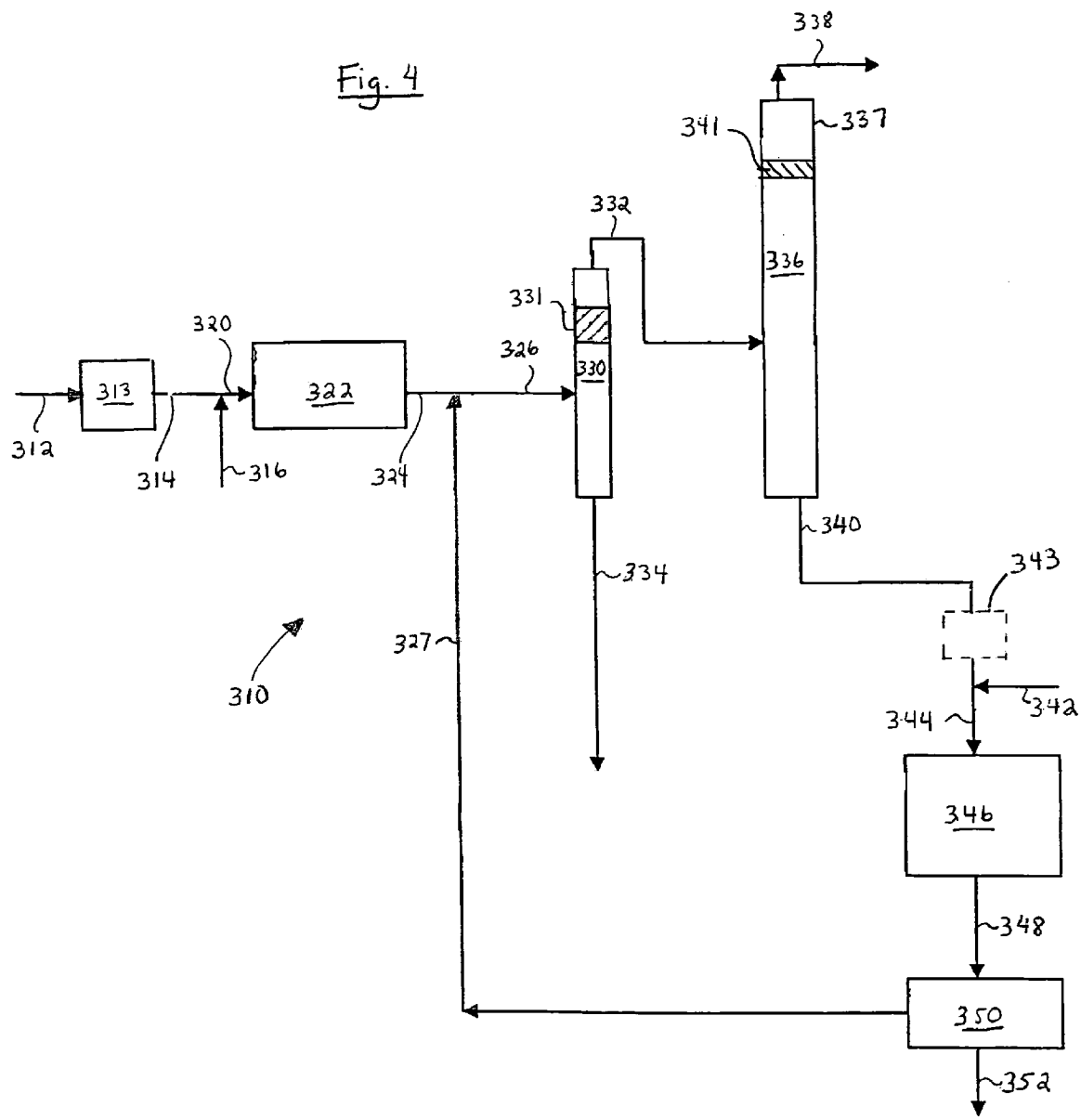
FIG. 4 is a schematic drawing of another embodiment in which a 2-butene stream is produced and used as the feed stream in a metathesis reaction.

FIG. 4 depicts a system 310 for producing propylene from a C4 stream. A C4 feed stream 312 is passed though a selective hydrogenation unit 313 which hydrogenates butadiene in the presence of a hydrogenation catalyst, producing a low-butadiene C4 feed stream 314. A hydrogen stream 316 is combined with stream 314 to form stream 320. Stream 320 is fed to a fixed bed hydroisomerization reactor 322 in which 1-butene is hydroisomerized into 2-butene. As an alternative, streams 314 and 316 can be separately fed to the hydroisomerization reactor 322. The effluent stream 324 is combined with a metathesis recycle stream 327 to form stream 326, which is fed to a fractionating tower 330. The effluent stream 324 optionally may be vented to remove excess hydrogen from the stream before being combined with the recycle stream 327. In fractionating tower 330, C4 compounds are removed from the top in stream 332 and C5+ compounds are removed as bottoms in stream 334. A hydrogenation catalyst bed 331, also known as a "guard bed", hydrogenates remaining butadienes to form butenes.

Stream 332 is subsequently fed to a deisobutylenizer tower 336. Above the feed point in deisobutylenizer tower 336, there is an elevation at the upper end 337 of the deisobutylenizer tower 336 at which the concentrations of 1-butene is at a maximum if no catalyst section is included. A catalytic section 341 which preferably is a single catalyst bed is positioned at this location in order to hydroisomerize 1-butene to 2-butene. The top stream 338 from the deisobutylenizer tower 336 contains isobutylene and isobutane, and small quantities of 1-butene and 2-butene. The bottoms stream 340 contains the 2-butene. Stream 340 optionally is purified in one or more guard beds 343. An ethylene feed stream 342 is combined with the bottoms stream 340 to form a metathesis reactor feed stream 344. This stream enters the metathesis reactor 346, in which the 2-butene and ethylene react to form a metathesis product stream 348.

The metathesis product stream 348 contains propylene, butenes and C5+ hydrocarbons. The propylene is separated from the heavier hydrocarbons in separator 350 and is removed as the product in stream 352. The C4, C5 and heavier hydrocarbons are recycled in metathesis recycle stream 327 and are combined with the debutanizer feed from stream 324 in stream 326.

The inclusion of a single catalyst stage in the deisobutylenizer in the embodiments of FIGS. 1-4 allows for a slightly lower conversion of the feed 1-butene to 2-butene to be used in the hydroisomerization reactor, thereby resulting in a lower rate of conversion of butenes to butanes. As a result, more butenes exit from the deisobutylenizer, resulting in a higher rate of propylene production for a given quantity of C4 feed. The majority of the 1-butene is still converted in the fixed bed hydroisomerization reactor for reasons that will be illustrated in the example.

The invention is particularly useful for processing stream cracker C4 streams and refinery C4 streams. Typically, steam cracker C4 streams contain appreciable quantities of butadiene and therefore require inclusion of a selective hydrogenation unit to convert the majority of the butadiene to butenes upstream of the hydroisomerization reactor. Refinery C4 streams have a low butadiene content that can be processed within the hydroisomerization unit, and thus inclusion of a selective hydrogenation unit is not required. The inclusion of a fractionator upstream from the deisobutylenizer provides for the removal of heavy materials that enter the system along with the C4s. Refinery C4 streams often contain heavier sulfur compounds including dimethyl disulfide (DMDS) and diethyl disulfide (DEDS), both of which can be removed by a first fractionating tower, as is shown in FIGS. 2 and 4.

EXAMPLES

The examples show various processing options for a single C4 feed stream having the composition shown below on Table 1. This stream typically is generated from a steam cracker C4 stream. Alternately, the C4 stream could be from an FCC unit or could be a mixture of the two.

TABLE 1

| C4 LIQUID Feed | | |
|---|---|---|
| Feed Rate | kg/hr | 39317 |
| Molecular Weight | | 56.71 |
| | | wt % |
| Hydrogen | | 0.00 |
| Methane | | 0.03 |
| Propylene | | 0.33 |
| Propane | | 0.85 |
| 13 Butadiene | | 0.13 |
| 1-Butene | | 11.63 |
| Cis-2-Butene | | 9.66 |
| Trans-2-butene | | 15.97 |
| Isobutylene | | 18.73 |
| Isobutane | | 28.57 |
| n-Butane | | 14.02 |
| n-Pentane | | 0.08 |
| Total | | 100.00 |

The methane is soluble methane from an upstream selective hydrogenation unit where the butadiene has been reduced from approximately 45,000 ppmw (parts per million based on weight) in the feed to 1300 ppmw in the effluent using a hydrogen stream that contains some quantity of methane. As a result of the selective hydrogenation step, the total 2-butenes are 26.63 wt % and the 1-butene is 11.63 wt %. This results in a 2-butene to 1-butene ratio of 2.29. This is far from the hydroisomerization equilibrium ratio at the nominal hydroisomerization reactor temperature of 60 deg. C. At 60 deg. C., the equilibrium ratio of 2-butene to 1-butene is 21.6.

The hydrogen used in the examples consists of a mixture of 95 wt. % hydrogen and 5 wt. % methane, with a molecular weight of 2.11.

In the fixed bed hydroisomerization reactor, the 1-butene is reacted to form 2-butene and the remaining butadiene is hydrogenated to 1-butene. There is also reaction of the 1-butene in the feed (and/or 1-butene formed from butadiene) to n-butane. The selectivity is defined as that portion of the 1-butene converted that is converted to n-butane. In this particular example, the equilibrium mixture of 1-butene and 2-butene would result in the conversion of 84.9% of the 1-butene. Note that complete conversion can not be obtained in a single step due to the limitation of equilibrium.

Figure 5:
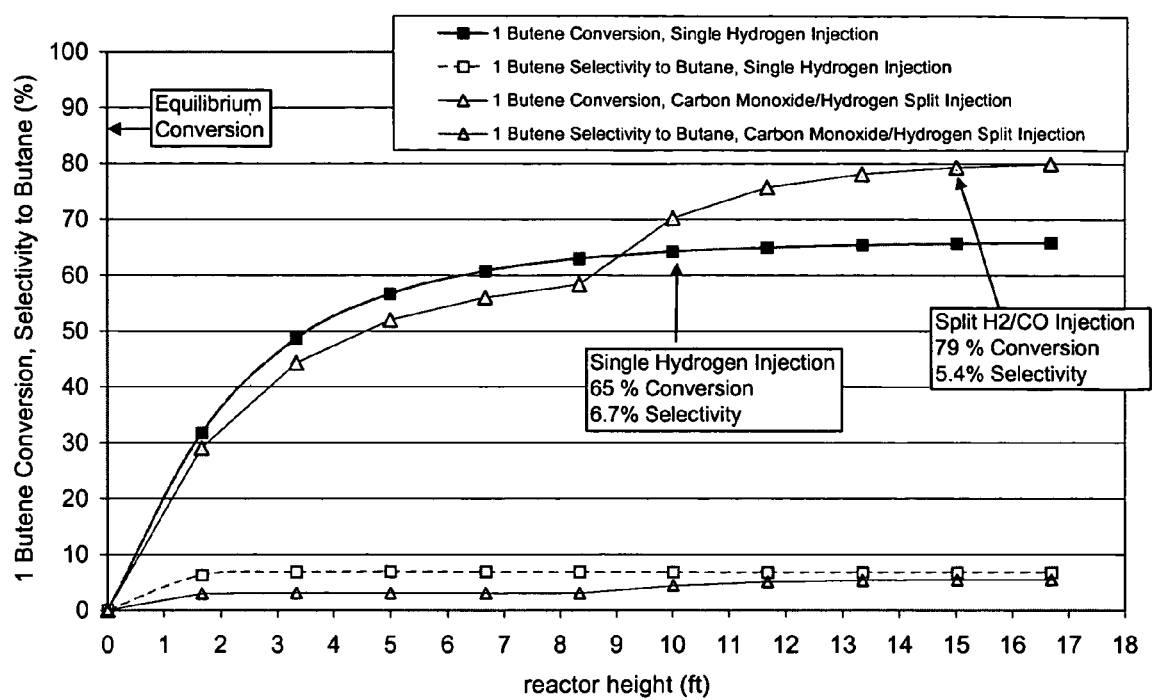
FIG. 5 is a graph showing the conversion and selectivity profiles for the hydroisomerization of 1-butene to 2-butene.

FIG. 5 shows the conversion/selectivity for reaction of a C4 stream over a hydroisomerization reactor containing a supported Pd catalyst. FIG. 5 shows the performance when using a single pure hydrogen feed and the improvement which can result from the use of small quantities of CO with hydrogen injected at multiple feed points in the hydroisomerization reactor. When a single hydrogen injection point is used in a 10 ft. L×4.5 ft. ID hydroisomerization reactor, the conversion to 1-butene is 65% with a selectivity to n-butene of 6.7%. Selectivity to butane is defined as the total butane produced divided by the 1-butene converted. As described above, under normal conditions, butane is formed simultaneously as the 1-butene is hydroisomerized to 2-butene. When two hydrogen/CO feeds are used, the rate of reaction is suppressed slightly and the selectivity to butane is reduced. A 15 ft. L×4.5 ft. ID hydroisomerization reactor containing more catalyst is used and the conversion improves to 79% with 5.4% selectivity to n-butane. For the feedstock shown and for the temperature of the reactor, the equilibrium conversion (without hydrogenation to butane) is 84.9%.

Figure 6:
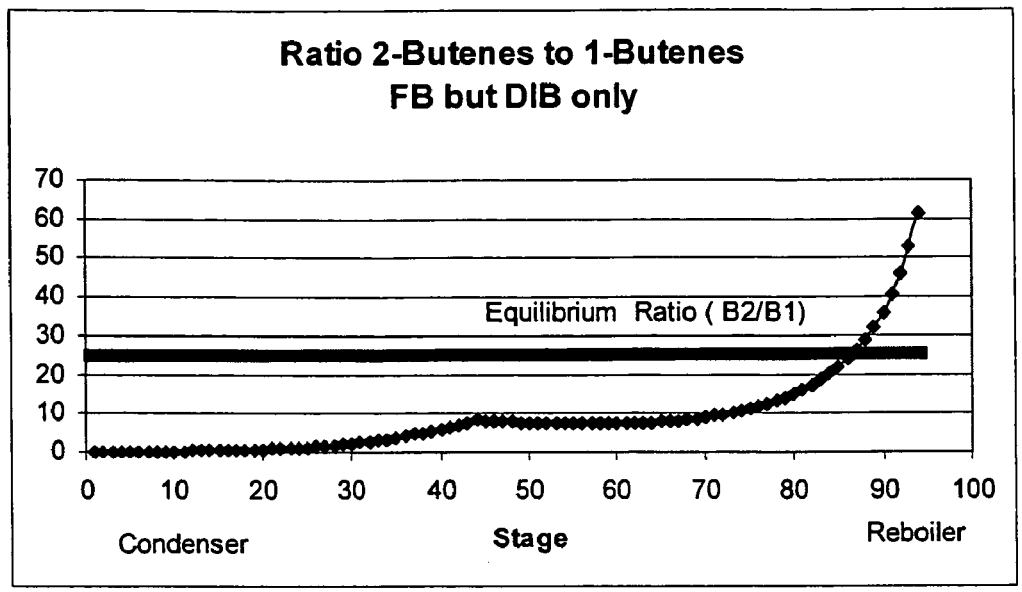
FIG. 6 is a graph showing the ratio of 1-butenes to 2-butenes in a deisobutylenizer which is downstream from a fixed bed reactor.

It is important to define the proper location for the catalyst stage in the deisobutylenizer. The location preferably is the point of maximum driving force for the hydroisomerization reaction. This location is defined by considering the composition profiles of the tower using a fixed bed only (no catalyst stage in the DeIB). The composition profile over the DeIB for Comparative Example 1 is shown in FIG. 6. As can be seen, for most of the tower, the ratio is below equilibrium indicating potential favorable reaction of 1-butene to 2-butene. This is the result of the 2-butene being fractionated away and moving to the bottom portion of the tower.

Figure 7:
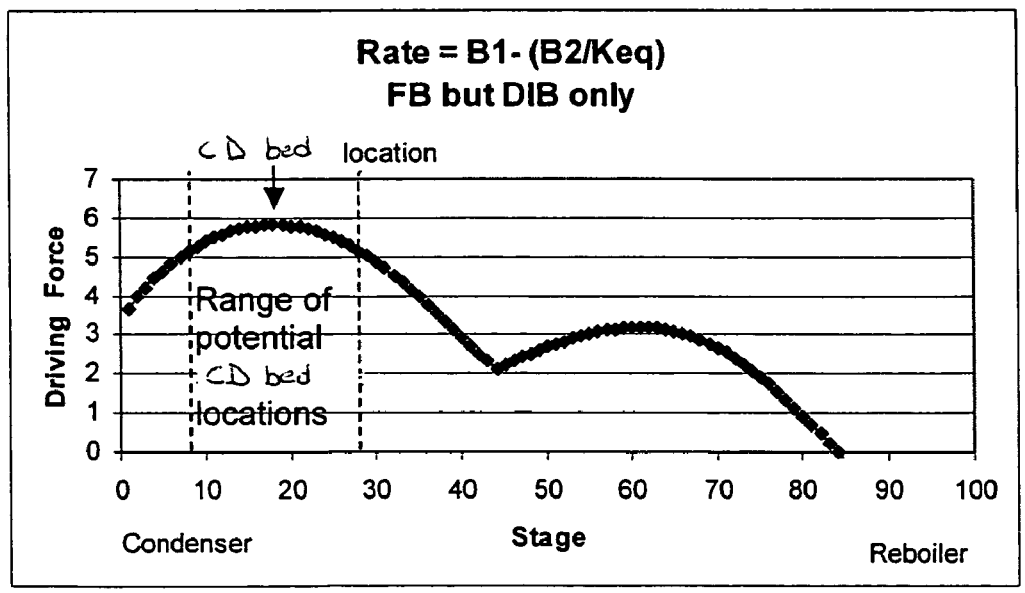
FIG. 7 is a graph showing the driving force at various stages in a deisobutylenizer which does not have a catalytic distillation stage in the fractionation column.

FIG. 7 shows the 'driving force' as defined. As can be seen, the potential locations for the catalyst stage are between stages 9 and 29 with the optimal location at stage 18. This location will vary dependent upon the specifics of the feedstock and fractionation operating conditions. It is however desired that the location be at or near the point of optimal driving force with preferred locations having driving forces at least 85% of the maximum, and more preferably 90% of the maximum, as defined by the composition profile without a catalyst stage in the DeIB. Typically, at least 50% of the 1-butene conversion occurs in the fixed bed reactor and the remaining conversion occurs over the second hydroisomerization catalyst.

Example 1 (Comparative)

Conventional CD-DeIB Tower

A sophisticated computerized simulation was run in which feed streams having the composition shown above were sent to three different conventional CD DeIB towers. A total of 10109 lb/hr of 1-butene is in the feed. In addition there is 22235 lb/hr of 2-butene and 116 lb/hr of butadiene. The first tower, Tower 1A, consisted of 94 equilibrium stages and a reflux ratio of 4.5 (reflux to feed). This tower contained 23581 lb of catalyst in 2042 ft$^3$ of catalytic distillation structures. This represents approximately space velocity of 2.3 weight catalyst per weight of 1 butene fed to the tower. The balance of the tower was filled with high efficiency fractionation packing. Hydrogen was added below the catalyst beds and below the feed to supply the required hydrogenation of butadiene and 1 butene hydroisomerization. The second tower, Tower 1B, consisted of 129 equilibrium stages and had a reflux ratio of 4.5 (reflux to feed). The additional 35 stages helped to achieve better separation. This tower also contained 23581 lb of catalyst in 2042 ft$^3$ of structures. The balance of the tower was filled with high efficiency fractionation packing. Hydrogen was added to supply the required hydrogenation of butadiene and 1-butene hydroisomerization. The third tower, designated as Tower 1C, consisted of 94 equilibrium stages and operated at a reflux ratio of 6.20 (reflux to feed). The higher reflux improved fractionation but required more utilities (reboiling and condensing duty). This tower also contained 23581 lb of catalyst in 2042 ft$^3$ of structures. The balance of the tower was filled with high efficiency fractionation packing. Hydrogen was added to supply the required hydrogenation of butadiene and 1-butene hydroisomerization.

In a CD-DeIB tower of the prior art, fractionation and hydroisomerization proceed in parallel. Over a multiplicity of stages, the 1-butene reacts to form 2-butene while simultaneously the 2-butene moves downward by fractionation and the 1-butene moves upward by fractionation. Thus, as the mixture moves upward through the tower, the reaction mixture is continually moving away from equilbrium by fractionation and toward equilibrium via reaction. In order to achieve high conversion, a multiplicity of reaction stages are required to match the multiplicity of fractionation stages. This results in a large amount of catalyst. This sequence occurs in all three towers.

In all of the three towers, the feedstock is as shown in Table 1. There is a considerable amount of 1-butene and butadiene in the feed. It is the objective of the design to produce a bottoms stream containing a high fraction of 2-butene and minimal amount of butadiene. As discussed above, the 1-butene tends to rise in the tower and the butadiene tends to move lower. This impacts the performance of the tower in that fractionation conditions must be varied to achieve a mixture with low butadiene.

As is shown on Table 2, in Tower 1A there was insufficient fractionation to achieve a high recovery of n-butenes in the bottoms as desired for a metathesis process. Since the feed to the tower is unreacted, the overhead product rate had to be increased to move the butadiene up the tower and thus over the hydrogenation/hydroisomerization catalyst. This was required to reduce the butadiene in the effluent to 10 ppm. With the higher overhead product flow, significant 2-butene was lost overhead. The recovery was 76.1% of the feed as n-butenes in the bottoms when meeting a low butadiene level in the bottoms product. Significan 2-butene was lost overhead. It is also important to note that when the butadiene must be pushed overhead a greater amount of hydrogenation occurs resulting in a higher selectivity to butane. This is undesirable.

In Tower 1B, an increased number of fractionation stages (129 versus 94) were used to improve recovery. The recovery increased to 91%. This option required more capital cost in the fractionation tower.

Tower 1C used reflux to improve fractionation performance. In this case, a higher reflux ratio (6.2 versus 4.5) was used. This improved the recovery to 93.8%. However, this option required more capital cost due to the higher traffic in the tower needed a larger tower diameter. Further, the energy requirement was greater due to the higher reboiler and condenser duties.

TABLE 2

| | | Example Number | | |
|---|---|---|---|---|
| | | Comp. 1A | Comp. 1B | Comp. 1C |
| Number of Stages | | 94 | 129 | 94 |
| Reflux Rate | lb/hr | 400000 | 400000 | 550000 |
| Total Feed Rate | lb/hr | 88689 | 88689 | 88689 |
| % Feed nButenes in Bottoms | wt % | 76.10 | 91.25 | 93.80 |
| i-butylene in Bottoms, | wt % | 0.06 | 0.02 | 0.05 |
| 13 BD in Bottoms | ppmw | 10 | 10 | 10 |
| 1-Butene in Distillate | lb/hr | 1535 | 1135 | 984 |
| 2-Butenes in Distillate | lb/hr | 5104 | 1588 | 899 |
| 1-Butene in Bottoms | lb/hr | 24 | 15 | 23 |
| 2-Butenes in Bottoms | lb/hr | 24596 | 29498 | 30318 |
| Selectivity to N butane (Saturation) | % | 13.5 | 2.4 | 2.5 |
| Conversions and Selectivity | | | | |
| 1-Butene in | lb/hr | 10109 | 10109 | 10109 |
| 1-Butene out | lb/hr | 1586 | 1154 | 1011 |
| 1-Butene Conversion | wt % | 84 | 89 | 90 |
| n-Butane in | lb/hr | 12174 | 12174 | 12174 |

TABLE 2-continued

| | | Example Number | | |
|---|---|---|---|---|
| | | Comp. 1A | Comp. 1B | Comp. 1C |
| n-Butane out Utilities | lb/hr | 13327 | 12389 | 12400 |
| Reboiler | MMkcal/hr | 17.54 | 17.02 | 22.30 |
| Condenser Catalyst | MMkcal/hr | 17.11 | 16.69 | 21.70 |
| Catalyst Amount (Tower) | lb | 23581 | 23581 | 23581 |
| Catalyst Volume (Structure) | ft3 | 2042 | 2042 | 2042 |

Example 2

A sophisticated computerized simulation was run in which a feed stream having the same composition of the feed streams used in Comparative Example 1 was sent to a 10 ft L×4.5 ft ID fixed bed hydroisomerization unit. Following the fixed bed, the effluent flowed to a fractionation tower to separate the isobutylene and isobutane from the 2-butene and n-butane. No catalyst is employed in the fractionating tower. The tower following the fixed bed consisted of 94 theoretical stages with a reflux ratio of 4.5. The simulated reactor was a fixed bed with a single hydrogen feed (no CO) and had 6.7% 1-butene saturation as shown in FIG. 5. The reboiler and condenser duties were equivalent to those of CD-DeIB Tower 1A in Comparative Example 1 since they are set by the reflux ratio. The process resulted in a 65% conversion of 1-butene (Comparative Example 2). The results are shown on Table 3. The overall recovery of normal butenes (1-butene and 2-butene) is 90.3%. The principal loss of total normal butenes is the loss of 1-butene in the overhead due to the lower 1-butene conversion using a fixed bed reactor only. This recovery is however higher than the CD-DeIB under the same fractionation conditions due to the higher 2-butene and lower 1-butene and butadiene content of the feed to the fractionation tower resulting from the conversion in the fixed bed reactor. This performance is representative of the performance of the prior art fixed bed plus fractionation tower system.

Example 2A

Catalyst Stage Added to Deisobutylenizer; Single Feed of Hydrogen used in Hydroisomerization Reactor The procedure of Comparative Example 2 was repeated with the exception that a single catalyst stage was added near the top of the fractionation tower, at stage 18. This resulted in an improvement in the % feed of n-butenes in the bottoms from 90.3% (Comparative Example 2) to 97.96% (Example 2A). In this example, the fixed bed hydroisomerization reactor using a single hydrogen feed (and no CO) was used to convert 66% of the 1-butene to 2-butene (and n-butane). Following the fixed bed, the feedstock mixture consisted of 3521 lb/hr 1-butene, 29179 lb/hr 2-butene, and 1.2 lb/hr butadiene. By incorporating a single catalyst stage at the proper location within the tower, an additional 2602 lb/hr of 1-butene is converted. This raises the overall conversion to 91%. Further, given the composition of the feedstock entering the tower, there are favorable fractionation conditions that result in high recovery (97.96%) of total normal butenes without having to utilize additional fractionation trays or higher reflux.

Example 2B

Catalyst Stage Added to Deisobutylenizer; Split Feed of Hydrogen and CO used in Hydroisomerization Reactor The procedure of Example 2A was repeated with the exception that a combined feed of hydrogen and CO was added at two different locations along the length of the hydroisomerization reactor, and the simulated reactor was a fixed bed using two hydrogen/CO feeds to realize 79% conversion in the fixed bed with 5.4% 1-butene saturation. This is Example 2B. The results are shown on Table 3 below.

TABLE 3

| | | Example Number | | |
|---|---|---|---|---|
| | | Comp. 2 | 2A | 2B |
| $H_2$ PP top bed | | — | 0.05 | 0.05 |
| Reflux Rate | lb/hr | 400000 | 400000 | 400000 |
| Total Feed Rate | lbs/hr | 88689 | 88689 | 88689 |
| % Feed n-Butenes in Bottoms | wt % | 90.33 | 97.96 | 98.2 |
| i-Butylene in Bottoms, | wt % | 3.55 | 3.97 | 3.95 |
| 1,3 Butadiene in Bottoms | ppmw | 10 | 10 | 10 |
| 1-Butene in Distillate | lb/hr | 2706 | 191 | 149 |
| 2-Butenes in Distillate | lb/hr | 117 | 129 | 99 |
| 1-Butene in Bottoms | lb/hr | 770 | 683 | 407 |
| 2-Butenes in Bottoms | lb/hr | 28447 | 31005 | 31356 |
| 1,3 Butadiene Conversion | wt % | 99 | 99 | 99 |
| Overall Conversion & Selectivity | | | | |
| 1-Butene in | lb/hr | 10109 | 10109 | 10109 |
| 1-Butene out | lb/hr | 3476 | 874 | 556 |
| 1-Butene Conversion | wt % | 65 | 91 | 94 |
| n-Butane in | lb/hr | 12174 | 12174 | 12174 |
| n-Butane out | lb/hr | 12613 | 12646 | 12641 |
| Selectivity to n-Butane (Saturation) | wt % | 6.6 | 5.1 | 4.9 |
| Fixed Bed Outlet Composition | | | | |
| 1 3-Butadiene | wt % | 13 ppm | 13 ppm | 13 ppm |
| Isobutane | wt % | 28.56 | 28.56 | 28.56 |
| Isobutylene | wt % | 18.72 | 18.72 | 18.72 |
| 1 Butene | wt % | 3.97 | 3.97 | 2.36 |
| 2 Butenes | wt % | 32.9 | 32.9 | 34.54 |
| n-butane | wt % | 14.52 | 14.52 | 14.52 |
| 1-Butene Conversion (FB only) | % | 66 | 66 | 80 |
| Catalyst | | | | |
| Catalyst Amount (Fixed Bed Plus Tower) | lb | 8160 | 14055.3 | 18135.4 |
| Catalyst Volume (Fixed Bed) | ft3 | 160 | 160 | 240 |
| Catalyst Volume in Tower (Structure) | ft3 | — | 510.4 | 510.4 |

Examples 2A and 2B show improved performance compared to catalytic distillation (CD-DeIB) Tower 1A of Comparative Example 1 and the fixed bed conventional tower system (Comparative Example 2). The recovery is significantly higher at equivalent fractionation conditions. Further, compared to the CD-DeIB, catalyst volumes are much lower. The split $H_2$/CO case increases the recovery to 98.2% (Example 2B) from 97.96% (Example 2A) as a result of the lower losses of butenes to n-butane (improved selectivity). While this Example requires more catalyst than Example 2A, both Example 2A and Example 2B require substantially lower catalyst quantities than the CD-DeIB cases of Comparative Example 1. The fixed bed accomplished the bulk of the hydroisomerization reaction. When using two hydrogen/CO feeds in the fixed bed, the conversion was 79% at a butane selectivity of 5.4%. The single catalyst stage increased the conversion since there had been separation of 1-butene from 2-butene in the tower allowing for additional reaction in the catalyst section. That portion of the 1-butene reaction proceeded with minimal hydrogenation and thus the overall selectivity is decreased to 4.9%.

As can be seen, the use of a single catalyst stage in the deisobutylenizer results in higher n-butene recovery than the cases with a fixed bed only followed by a conventional DeIB tower. In all cases, the catalyst costs for the fixed bed options are lower than for Comparative Example 1. The point of maximum hydroisomerization driving force makes maximum utilization of the single catalyst section.

In summary, the comparisons at the same fractionation conditions (94 theoretical trays and reflux ratio=4.5) are shown in Table 4 for the case with 10 ppm butadiene in the bottoms:

TABLE 4

| | Case | | |
|---|---|---|---|
| | Comp. Ex. 2 Fixed bed only | Comp. Ex. 1A CD DeIB | Ex. 2B Fixed bed with split $H_2$/CO feeds and 1 catalyst section in DelB |
| N-Butene Recovery | 90.33 Some improvement possible with increased stages and/or reflux | 76.10 Can improve to 93% with increased stages (35 more) or reflux (38% more) | 98.2 Some increase possible with stages and reflux but diminishing returns |

As will be apparent to persons skilled in the art, various of the above-disclosed and other features and functions, or alternatives thereof, may be desirably combined into many other different systems or applications. Furthermore, various presently unforeseen or unanticipated alternatives, modifications, variations or improvements therein may be subsequently made by those skilled in the art which are also intended to be encompassed by the following claims.

What is claimed is:

1. A process for the preferential conversion to 2-butene of a C4 stream containing 1-butene and 2-butene, comprising:
   mixing said C4 stream with a first hydrogen stream to form a feed stream,
   hydroisomerizing said feed stream in the presence of a first hydroisomerization catalyst in order to convert at least a portion of said 1-butene to 2-butene and to produce a hydroisomerization effluent,
   separating said hydroisomerization effluent in a catalytic distillation column having an upper end and a lower end to obtain a 1-butene mixture at said upper end, a top effluent stream comprising isobutane and isobutylene and a bottoms stream comprising 2-butene, and
   hydroisomerizing said 1-butene mixture at said upper end of said catalytic distillation column using a second hydroisomerization catalyst to obtain additional 2-butene in said bottoms stream,
   wherein said second hydroisomerization catalyst is in the form of catalytic distillation structure for concurrent reaction and separation and is located within said upper end as a single reaction stage proximate an elevation of maximum 1-butene concentration determined as if said step of hydroisomerizing using second hydroisomerization catalyst were eliminated.

2. The process of claim 1, wherein said C4 stream contains butadiene, further comprising hydrogenating the C4 stream to reduce the butadiene content to no more than about 1 wt % prior to hydroismerizing said feed stream.

3. The process of claim 1, wherein said second hydroisomerization catalyst is positioned at an elevation in said column at which the 1-butene to 2-butene molar ratio would be at a maximum if no second hydroisomerization catalyst were present.

4. The process of claim 1, wherein said second hydroisomerization catalyst is located within the catalytic distillation column.

5. The process of claim 4, where the catalyst is positioned within distillation structures.

6. The process of claim 1, further comprising mixing said bottoms stream with a suitable metathesis reactant to form a metathesis feed stream, feeding said metathesis feed stream to a metathesis reactor, and reacting said 2-butene with said metathesis reactant to form a metathesis product.

7. The process of claim 6, wherein said metathesis reactant comprises ethylene and said metathesis product comprises propylene.

8. The process of claim 1, wherein said feed stream includes C5 and heavier components, further comprising removing said C5 and heavier components from said hydroisomerization effluent before separating said hydroisomerization effluent in said catalytic distillation column.

9. The process of claim 6, further comprising purifying one of said bottoms stream and said metathesis feed stream before feeding said metathesis feed stream to said metathesis reactor.

10. The process of claim 1, further comprising feeding a second hydrogen stream to said hydroisomerization reactor at a location downstream from the feed point of said first hydrogen stream.

11. The process of claim 10, further comprising feeding a third hydrogen stream to said hydroisomerization reactor at a location downstream from the feed point of said second hydrogen stream.

12. The process of claim 1, wherein said first hydrogen stream further comprises carbon monoxide.

13. The process of claim 10, wherein the second hydrogen stream further comprises carbon monoxide.

14. The process of claim 11, wherein the second hydrogen stream further comprises carbon monoxide.

15. The process of claim 6, further comprising separating said metathesis product from heavier components to form a heavy component stream and combining said heavy component stream with said hydroisomerization effluent.

16. The process of claim 1, wherein the second hydroisomerization catalyst is positioned at an elevation in said catalytic distillation column at which the driving force for the hydroisomerization of 1-butene to 2-butene would be at least 85% of the maximum driving force within said column if no recycle stream were withdrawn.

17. The process of claim 1, wherein the second hydroisomerization catalyst is positioned at an elevation in said catalytic distillation column at which the driving force for the hydroisomerization of 1-butene to 2-butene would be at least 90% of the maximum driving force within said column if no recycle stream were withdrawn.

18. The process of claim 1, wherein at least 50% of the 1-butene conversion occurs in a fixed bed reactor containing the first hydroisomerization catalyst upstream of the catalytic distillation column containing the second hydroisomerization catalyst and the remaining conversion occurs over the second hydroisomerization catalyst.

19. The process of claim 1 where the first hydroisomerization catalyst comprises a group VIIIA metal on a support.

20. The process of claim 19, wherein the first hydroisomerization catalyst further comprises an additive selected from the group consisting of gold, silver and alkali metals.

21. The process of claim 1, wherein the second hydroisomerization catalyst comprises a group VIIIA metal on a support.

22. The process of claim 21, wherein the second hydroisomerization catalyst further comprises an additive selected from the group consisting of gold, silver and alkali metals.

23. A process for the production of propylene from a C4 stream containing butadiene, 1-butene and 2-butene, comprising:

mixing said C4 stream with a first hydrogen stream to hydrogenate butadiene and form a feed stream having a butadiene content of no more than 1 wt %, hydroisomerizing said feed stream in the presence of a first hydroisomerization catalyst in order to convert at least a portion of said 1-butene to 2-butene and to produce a hydroisomerization effluent while hydrogenating the butadiene, separating said hydroisomerization effluent in a catalytic distillation column having an upper end and a lower end to obtain a 1-butene mixture at said upper end, a top effluent stream comprising isobutane and isobutylene and a bottoms stream comprising 2-butene, hydroisomerizing said 1-butene mixture at said upper end of said catalytic distillation column using a second hydroisomerization catalyst to obtain additional 2-butene in said bottoms stream, mixing said bottoms stream with ethylene to form a metathesis feed stream, and feeding said metathesis feed stream to a metathesis reactor and reacting said 2-butene with said ethylene to form propylene, wherein said second hydroisomerization catalyst is in the form of catalytic distillation structure for concurrent reaction and separation and is located within said upper end as a single reaction stage proximate an elevation of maximum 1-butene concentration determined as if said step of hydroisomerizing using second hydroisomerization catalyst were eliminated.

* * * * *